(12) United States Patent
Shuler

(10) Patent No.: US 10,278,013 B2
(45) Date of Patent: Apr. 30, 2019

(54) PRESENCE ACTIVATED RADIO BEACON

(71) Applicant: Xicato, Inc., San Jose, CA (US)

(72) Inventor: John Hays Shuler, San Jose, CA (US)

(73) Assignee: Xicato, Inc., San Jose, CA (US)

( * ) Notice: Subject to any disclaimer, the term of this patent is extended or adjusted under 35 U.S.C. 154(b) by 0 days.

(21) Appl. No.: 15/941,759

(22) Filed: Mar. 30, 2018

(65) Prior Publication Data
US 2018/0288565 A1  Oct. 4, 2018

Related U.S. Application Data

(60) Provisional application No. 62/481,049, filed on Apr. 3, 2017.

(51) Int. Cl.
| | |
|---|---|
| *H04W 4/02* | (2018.01) |
| *H04W 4/06* | (2009.01) |
| *H04W 4/33* | (2018.01) |
| *H04W 4/80* | (2018.01) |
| *H04W 4/021* | (2018.01) |
| *H04W 52/02* | (2009.01) |

(52) U.S. Cl.
CPC ........... *H04W 4/021* (2013.01); *H04W 4/023* (2013.01); *H04W 52/0203* (2013.01); *H04W 4/02* (2013.01); *H04W 4/027* (2013.01); *H04W 4/06* (2013.01); *H04W 4/33* (2018.02); *H04W 4/80* (2018.02); *Y02D 70/00* (2018.01); *Y02D 70/142* (2018.01); *Y02D 70/144* (2018.01); *Y02D 70/164* (2018.01); *Y02D 70/20* (2018.01); *Y02D 70/22* (2018.01); *Y02D 70/26* (2018.01)

(58) Field of Classification Search
CPC ......... H04W 4/02; H04W 4/80; H04W 4/029; H04W 40/244; H04W 64/00; H04W 4/025; G06Q 30/0261; G06Q 30/0639; H04L 67/22; G08C 17/02; H04Q 2209/47; H04M 1/72572
See application file for complete search history.

(56) References Cited

U.S. PATENT DOCUMENTS

| | | | |
|---|---|---|---|
| 6,535,136 B1 * | 3/2003 | Rodenbeck | G06K 7/10128 235/382 |
| 9,913,086 B1 * | 3/2018 | Akhter | H04W 4/021 |
| 2013/0237240 A1 * | 9/2013 | Krantz | H04W 4/02 455/456.1 |
| 2015/0382385 A1 * | 12/2015 | Cai | H04W 76/021 370/254 |

(Continued)

*Primary Examiner* — Nizar N Sivji
(74) *Attorney, Agent, or Firm* — Silicon Valley Patent Group LLP

(57) ABSTRACT

A radio beacon device is configured to only transmit information about its location or information about the object the radio beacon is associated with when an occupant is present. For example, the radio beacon device may include a presence detector and may transmit the information only when the presence detector detects an occupant. In another example, the radio beacon device may remain in a low battery usage state until a presence detection message is received from a remote radio equipped presence sensor that is in proximity to the radio beacon device or a message is received from a mobile device in proximity to the radio beacon device. Once a presence detection message or message from a mobile device is received, the radio beacon device may transmit the information, e.g., for a predetermined amount of time.

22 Claims, 8 Drawing Sheets

(56) References Cited

U.S. PATENT DOCUMENTS

| | | | |
|---|---|---|---|
| 2016/0012381 A1* | 1/2016 | Hanson | G06Q 10/063116 |
| | | | 705/7.16 |
| 2017/0091699 A1* | 3/2017 | Mueller | G06Q 10/083 |
| 2017/0199874 A1* | 7/2017 | Patel | G06F 17/30041 |
| 2017/0300803 A1* | 10/2017 | Beavers | G06K 19/145 |
| 2018/0013815 A1* | 1/2018 | Gold | H04W 4/80 |
| 2018/0083943 A1* | 3/2018 | Bowman | G06F 21/62 |

\* cited by examiner

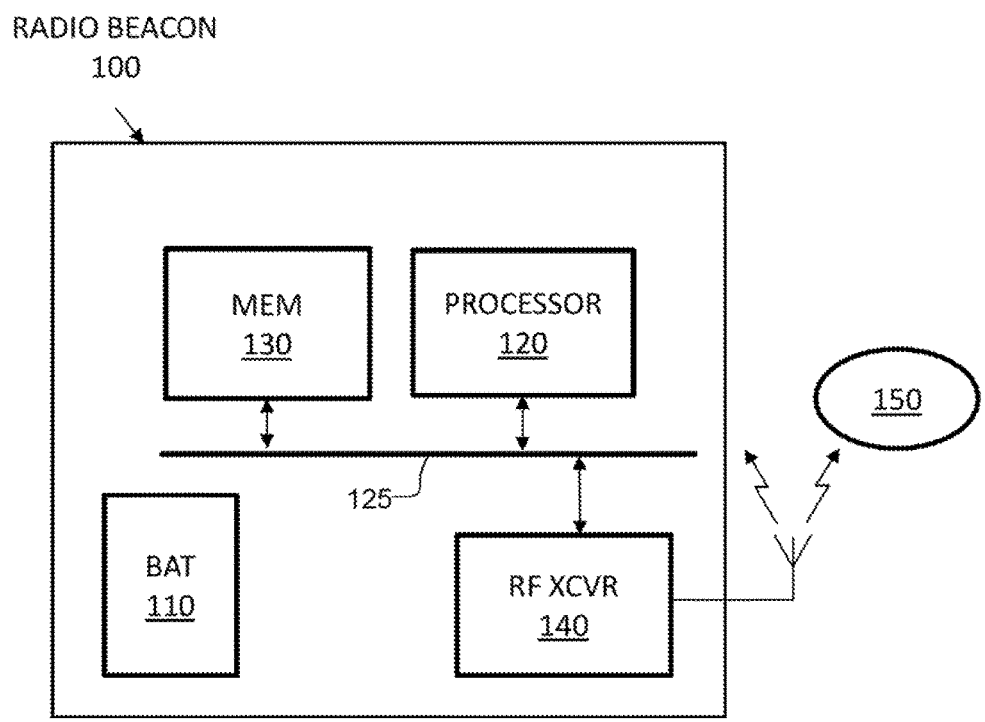
FIG. 1
(Conventional)

US 10,278,013 B2

PRESENCE ACTIVATED RADIO BEACON

CROSS REFERENCE TO RELATED APPLICATIONS

This application claims priority under 35 USC 119 to U.S. Provisional Application No. 62/481,049, filed Apr. 3, 2017, which is incorporated by reference herein in its entirety.

TECHNICAL FIELD

The described embodiments relate to digital radio transceiver devices, and in particular to low power radio transmission devices which are used to broadcast location information of transceiver device or information associated with an object associated with the radio transceiver.

BACKGROUND

Low power radio transceiver devices are starting to be used to enable location services, in particular for indoor use. Satellite positioning systems, such as the Global Positioning System (GPS) work well outdoors to determine accurate location data, but do not work well indoors as the signals from the satellites do not propagate well within the building environment.

Digital radio beacons may be used indoors to replace the function of the GPS satellites. Digital radio beacons, for example, may be placed at various locations in a building and transmit a message that allows an application on a smartphone to determine its location.

SUMMARY

A radio beacon device is configured to only transmit information about its location or information about the object the radio beacon is associated with when an occupant is present. For example, the radio beacon device may include a presence detector and may transmit the information only when the presence detector detects an occupant. In another example, the radio beacon device may remain in a low battery usage state until a presence detection message is received from a remote radio equipped presence sensor that is in proximity to the radio beacon device or a message is received from a mobile device in proximity to the radio beacon device. Once a presence detection message or message from a mobile device is received, the radio beacon device may transmit the information, e.g., for a predetermined amount of time.

In one implementation, a presence activated radio beacon device includes a presence detector configured to detect presence of an occupant in its proximity; a radio transceiver capable of broadcasting information associated with location or status of the presence activated radio beacon device; a memory configured to store an amount of information associated with the presence activated radio beacon device; and a processor configured to detect signals from the presence detector and to enable transmission from the radio transceiver.

In one implementation, a presence activated radio beacon device includes a radio transceiver capable of receiving presence detection information messages from radio equipped presence sensors in proximity to the presence activated radio beacon device and capable of broadcasting information messages; a memory configured to store an amount of information associated with the presence activated radio beacon device; a processor configured to process messages received by the radio transceiver, detect a presence detection information message from radio equipped presence sensors, and enable transmission of an information message from the radio transceiver in response to the detection of the presence detection information message.

In one implementation, a method of activating a presence activated radio beacon device includes entering a waiting state; detecting a presence detected radio message from a remote radio equipped presence sensor; broadcasting an information message in response to detecting the presence detected radio message; stopping the broadcast of the information message when no additional presence detected radio message is detected; and re-entering the waiting state.

Further details and embodiments and techniques are described in the detailed description below. The summary does not define the invention. The invention is defined by the claims.

BRIEF DESCRIPTION OF THE DRAWINGS

FIG. 1 is a schematic diagram of the components in a conventional low power radio beacon.

DETAILED DESCRIPTION

Figure 2:
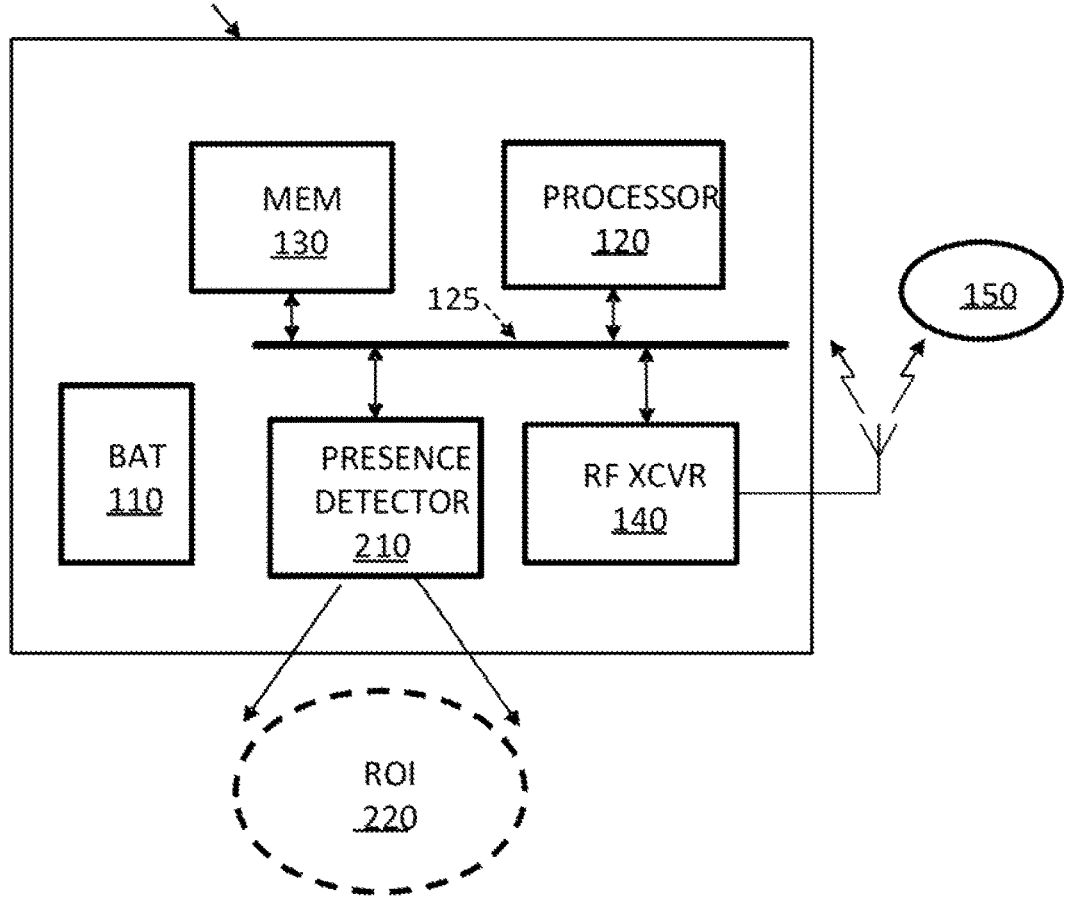
FIG. 2 is a schematic diagram illustrative of a radio beacon with integrated presence detector.

Reference will now be made in detail to background examples and some embodiments of the invention, examples of which are illustrated in the accompanying drawings.

To achieve high accuracy location determination using low power digital radio beacons, a dense network of beacons may be used. Placement of the beacons in key locations may also aid in achieving a desired accuracy of location determination. By way of example, a low power beacon may be placed behind a painting in a museum. The signal of such a beacon may be very low, such that only receivers within the range of a couple of meters are able to receive the signal. This allows an application on a mobile device, such as a smartphone, to supply detailed information about the painting, and to locate the application user within the museum facility.

To enable flexible placement of beacons in a space, the use of battery operated transmitters may be beneficial. Low power radio transmitters, such as Bluetooth Low Energy, are designed to last for an extended time on a battery, nevertheless, increasing runtime on a battery may be beneficial as battery replacement costs in a professional beacon installation application are high.

In addition to battery life, another concern in professional beacon installation applications is radio communication congestion. When many beacons are installed within a location and all of the beacons are continuously transmitting, the signals may interfere resulting in reception difficulties. This problem may be mitigated if beacons are active only when needed.

FIG. 1 is a schematic diagram of the components typically used in a radio beacon 100. Typically, such a device has a battery 110, and microprocessor 120, a computer memory 130 to store data, and to store series of processor instructions, and a radio transceiver 140. The battery supplies power to all the electronic components in this device. The power connections between the components are not illustrated in FIG. 1. Typically, additionally components, also not illustrated in FIG. 1, may be included radio beacon 100, e.g., between the battery 110 and the other components to control the voltages provided to each component, and to protect the other components from over voltage conditions. The electronic components are connected and can exchange data using a digital data bus 125, such as for example the I2C, SPI, or any other serial or parallel communications bus. Components 120, 130, and 140 are shown in this diagram as separate components, but some or all these might be integrated into one component or module in practice.

Different radio transceivers may be used that operate at various radio bands, but particularly interesting are radio transceivers that are used in smartphones, such as WiFi and Bluetooth radio transceivers. For low power beacons, especially Bluetooth Low Energy radio transceivers are frequently used, as they have a relatively long runtime on a battery. Such a transceiver will transmit, at regular time intervals, a digital radio message 150 containing information pertaining to the location of the beacon or to provide information of the object associated with the radio beacon.

There are various standards for the encoding of the radio packet transmitted by a radio transceiver: there is the iBeacon standard as defined by Apple, the Eddystone standard as defined by Google, and AltBeacon as defined by Radius Networks. All three standards use the Bluetooth Low Energy protocol, as defined and maintained by the Bluetooth Special Interest Group.

Battery operated radio beacons based on these standards are, for example, manufactured and sold by a company called Estimote. The battery life of such a device depends on the size of the battery, the advertising interval, broadcast power, and environmental conditions.

In professional applications many of these beacons may be used and a long runtime on a battery is highly desired. If, for example, typical runtime on a battery is 1 year, and an installation employs 1000 beacons, typically 20 batteries have to be replaced per week. If a runtime of 10 years can be achieved, 20 batteries per quarter have to be replaced which is more manageable and may be part of a regular maintenance program. While the use of battery 110 is illustrated herein, it should be understood that a wired power source may alternatively be used.

FIG. 2 is a schematic diagram illustrative of a first embodiment of a radio beacon 200 that includes a receiver of information that the presence of an occupant is detected. In the embodiment illustrated in FIG. 2, the receiver of the information that the presence of an occupant is detected is an integrated presence detector 210, which is digitally connected with the other component using digital bus 125, and may be powered using battery 110. If desired, the radio beacon 200 may be powered using wired power source.

Typically, Passive Infrared (PIR) motion sensors are used as presence detectors. These are, for example, produced by Panasonic of Japan, and have a low power consumption. The consumption current of a PIR sensor, for example, may be as low as 1 µA, which is a factor of 1000 to 10000 times lower than a transmitting Bluetooth transceiver which draws between 5 and 10 mA.

Other optical, microwave, or acoustic sensors, for example, may be used if desired, but passive sensors generally have a lower power consumption than active sensors.

A presence detector typically may be configured to detect presence or motion of an occupant within a Region Of Interest (ROI) 220, which includes selecting a viewing angle (narrow or broad) and/or distance. For a PIR sensor, configuration is done by choosing an appropriate type of lens for a desired application. The presence detector may detect the proximity of an occupant, which may be, e.g., a person, animal, or an object, such as a moving automated hospital cart or other mobile device. The distance that is considered proximate is dependent on the particular use case as will be understood by those skilled in the art. For example, if the use case is to provide an occupant with information about an object, e.g., in a museum, proximity may be a distance that is appropriate for association with that object, e.g., a few meters for association with a small object, or a greater distance for association with a room or building. If the use case is related to locating an occupant, proximity may be a distance that is appropriate for the desired resolution of position.

In normal operation of radio beacon 200, the radio transceiver 140 is switched off and the processor 120 will be in sleep mode. When the presence detector 210 detects motion or the presence of an occupant, it wakes up the processor 120, which will start to analyze the signals from the presence detector 210 and make sure that the presence detected is consistent. It will then assemble the broadcast message to be transmitted using the information stored on the memory chip 130, switch on the radio transceiver 140, which will broadcast the prepared message. The message, which may sometimes be referred to as a beacon, may include information related to the location or status of the radio beacon 200. Information related to the location and/or status of the radio beacon may be associated with a physical location, display or objects near to the radio beacon, or about displays or objects that a person is to find and inspect. For example, the message may be or may include an address or marker, such as an internet address, a GPS address or indoor location, or a message that is specific to the application in the receiving device. The message may be used for, e.g., determining an indoor location. It should be understood that the message does not have to include the location, but may be a pointer to the information either in an application on the mobile device or in the Internet. The message may additionally or alternatively be used for information delivery. Again, the message does not need to include the information but may be a pointer to the information either in an application on the mobile device or in the Internet. Thus, the message may include information about the location, e.g., information to determine a position of the receiving device or information associated with the location including objects present at the location. The use of the information in the message may be dependent on the particular application used on the receiving device and/or the occupants, which may be human or otherwise. Additionally, the message that is assembled may be context sensitive. For example, the message may be different based on the nature of the occupancy, such as whether the occupancy is detected based on received radio signals, motion, or based on a particular motion device or item that is detected.

The processor 120 keeps monitoring the presence detector 210 and as long as presence is detected it will keep the radio transceiver 140 running. When the presence detector 210 stops detecting presence the processor 120 will shut down the radio transceiver 140, and prepare itself to go in a sleep mode. The device can be configured to keep transmitting the information for some time after last presence was detected. Such a sustain time can be configured as a parameter and stored in the memory 130.

The radio transceiver 140 (or a separate receiver) may be configured to receive wireless signals to allow the beacon information stored in memory 130 to be altered (increased or decreased or otherwise modified), which may be performed dynamically.

Figure 3:
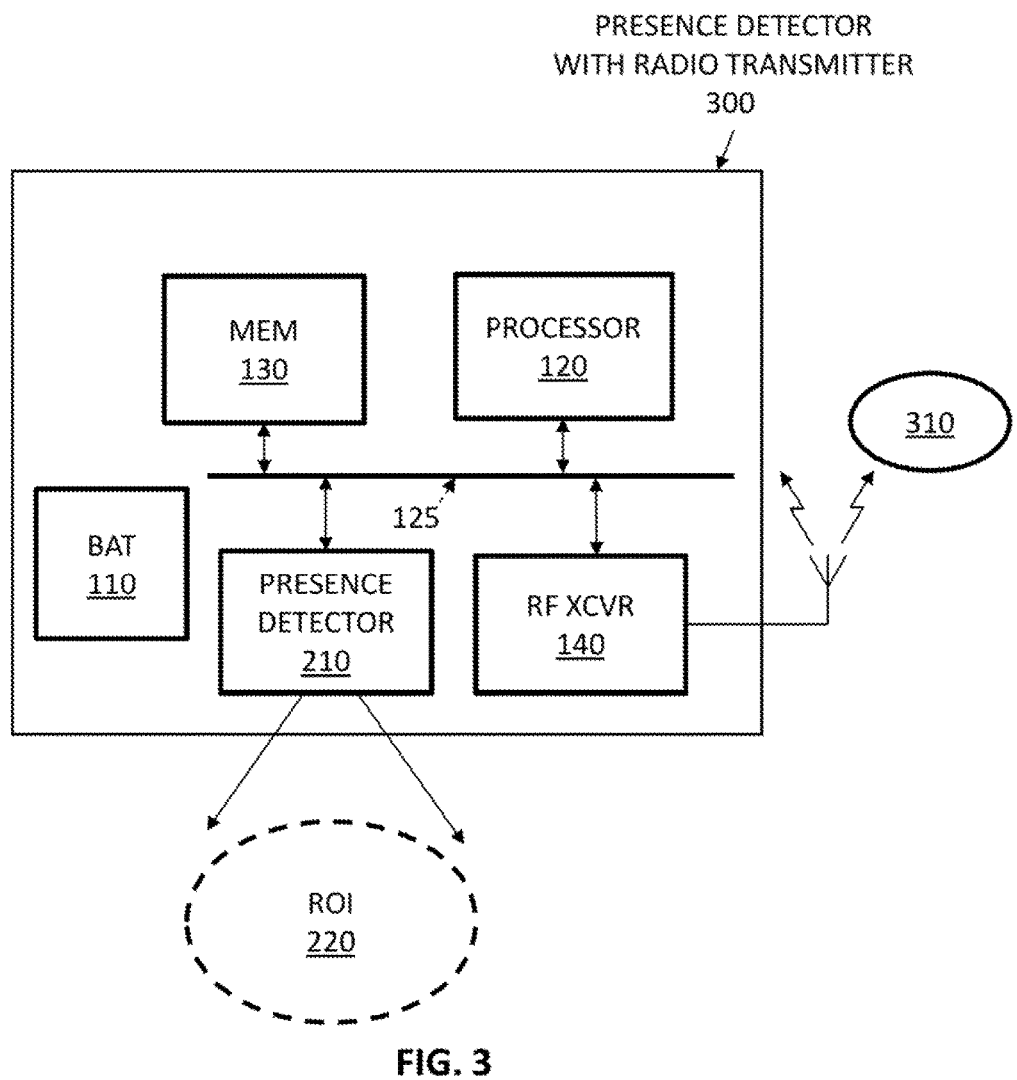
FIG. 3 is a schematic diagram of a presence detector equipped with a radio transmitter.

FIG. 3 is a schematic diagram of a presence detector 300 equipped with a radio transceiver 140, which is used in another embodiment of the invention. It differs from the low power radio beacon 200 as depicted in FIG. 2 by the fact that the radio transmission 310 from this device does not contain any information for users of a space, but only signals that occupancy is detected to other devices in a space such as low energy radio beacons which do not have their own occupancy sensor.

The presence detector 300 in this case is illustrated with a battery 110, but it may be attached to a wired power source, and for example be integrated in a lighting fixture.

Figure 4:
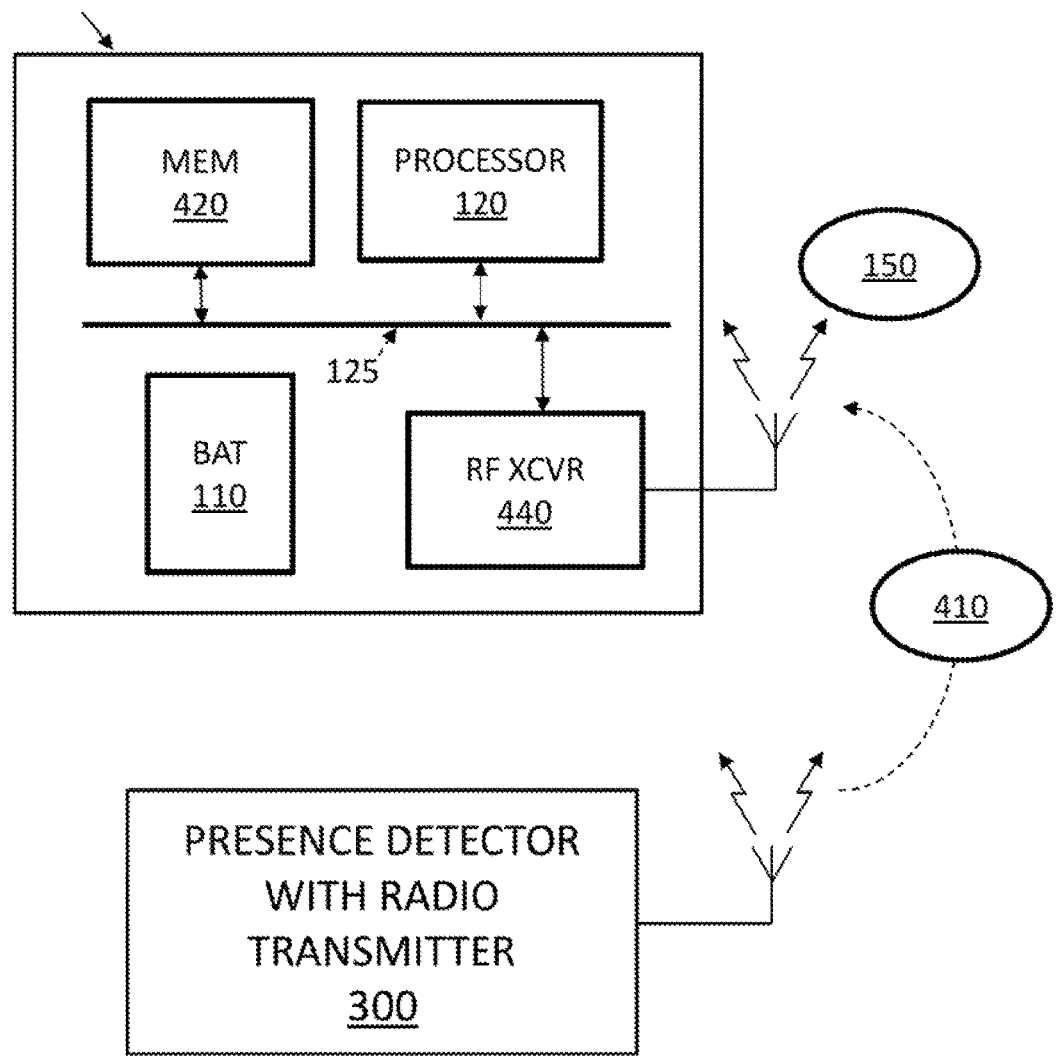
FIG. 4 shows a schematic diagram of a low energy radio beacon able to receive and transmit radio signals, a presence detector with radio transmitter, and transmission messages associated with the two devices.

FIG. 4 shows a schematic diagram of an embodiment of a low energy radio beacon 400 that is able to receive and transmit radio signals and includes a receiver of information that the presence of an occupant is detected. In the embodiment illustrated in FIG. 4, the receiver of the information that the presence of an occupant is detected is a radio transceiver 440 that is in wireless communication with the separate presence detector 300. Low energy radio beacon 400 differs from radio beacon 100 as depicted in FIG. 1 in that the radio transceiver 440 is in receive mode between the beacon broadcasts, while in FIG. 1 the transceiver 140 can be switched off between the beacon broadcasts. As with radio transceiver 140, the radio transceiver 440 (or a separate receiver) may be configured to receive wireless signals to allow the beacon information stored in memory 130 to be altered (increased or decreased or otherwise modified), which may be performed dynamically. Additionally, the processor instructions as stored on memory device 420 differ from the instructions as stored on memory device 130 as shown in FIG. 1. The presence detector 300 reports occupancy in a region of interest by transmitting a signal with a presence message 410, which are for example used by low energy radio beacons in its proximity.

The benefit of this embodiment is that not every beacon needs a presence detector, which reduces the cost of the radio beacons. The disadvantage of this approach is that the power consumption of the beacon is higher than with an integrated presence detector, as the radio has to check on a regular basis if presence is reported by a presence detector 300 in proximity. To mitigate or overcome this disadvantage, the presence detector 300 and the radio beacon 400 may synchronize their communication slots so that they are in sleep mode outside of these slots. Additionally, or alternatively, the presence detector 300 may be attached to a power supply, so that it does not run from a battery, and therefore is able to broadcast presence signals 410 over longer periods of time to make sure that beacons 400 will receive the presence signals 410 when they wake up from sleep mode.

Figure 5:
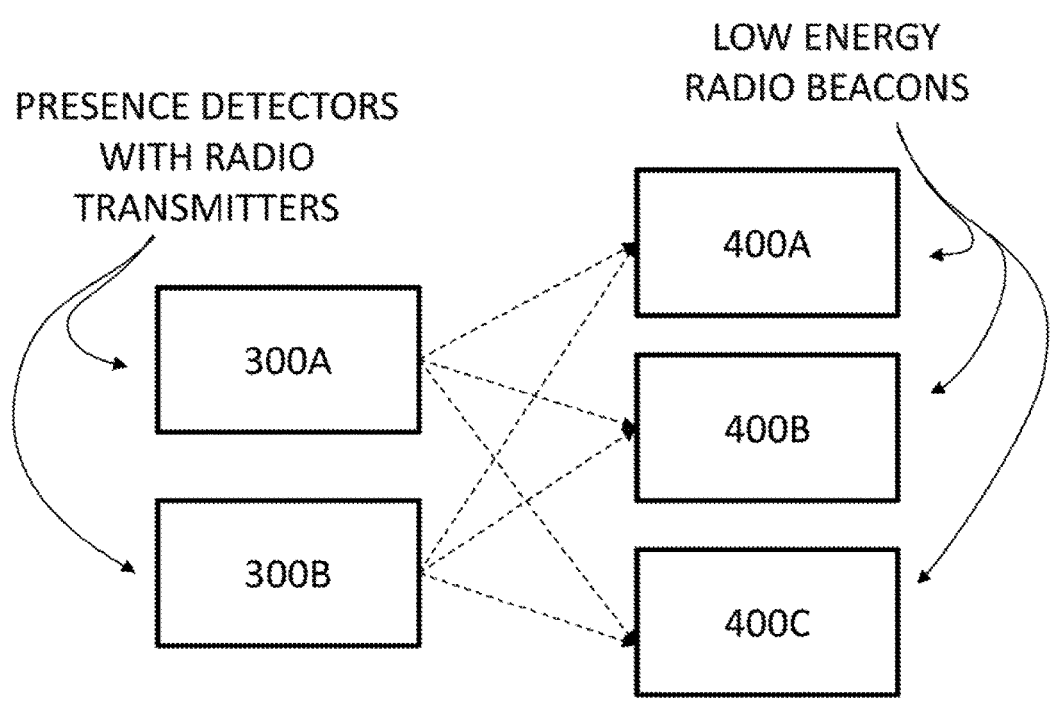
FIG. 5 is a diagram showing two transmitters and three low energy beacons equipped with radio transceivers and illustrating how the low energy beacons are associated with the presence detectors.

FIG. 5 is a diagram showing two presence detectors 300A and 300B (collectively sometimes referred to as presence detectors 300) and three low energy radio beacons 400A, 400B, and 400C (collectively sometimes referred to as low energy radio beacons 400) equipped with radio transceivers, and illustrates how the low energy radio beacons 400 are associated with the presence detectors 300. This configuration may be beneficial if there are more low energy radio beacons 400 than presence detectors 300 in an installation, or if the presence detector 300 are mounted at preferential locations compared to the radio beacons 400. Presence detectors 300, for example, might be mounted near entrances of a space, while the low energy radio beacons 400 might be mounted attached to objects located in the space.

Radio transmission presence packets emitted from presence detector 300A may be received by all low energy radio beacons 400A, 400B, and 400C. Also the radio transmission presence packets from 300B may be received by all low energy radio beacons 400A, 400B, and 400C.

Figure 6:
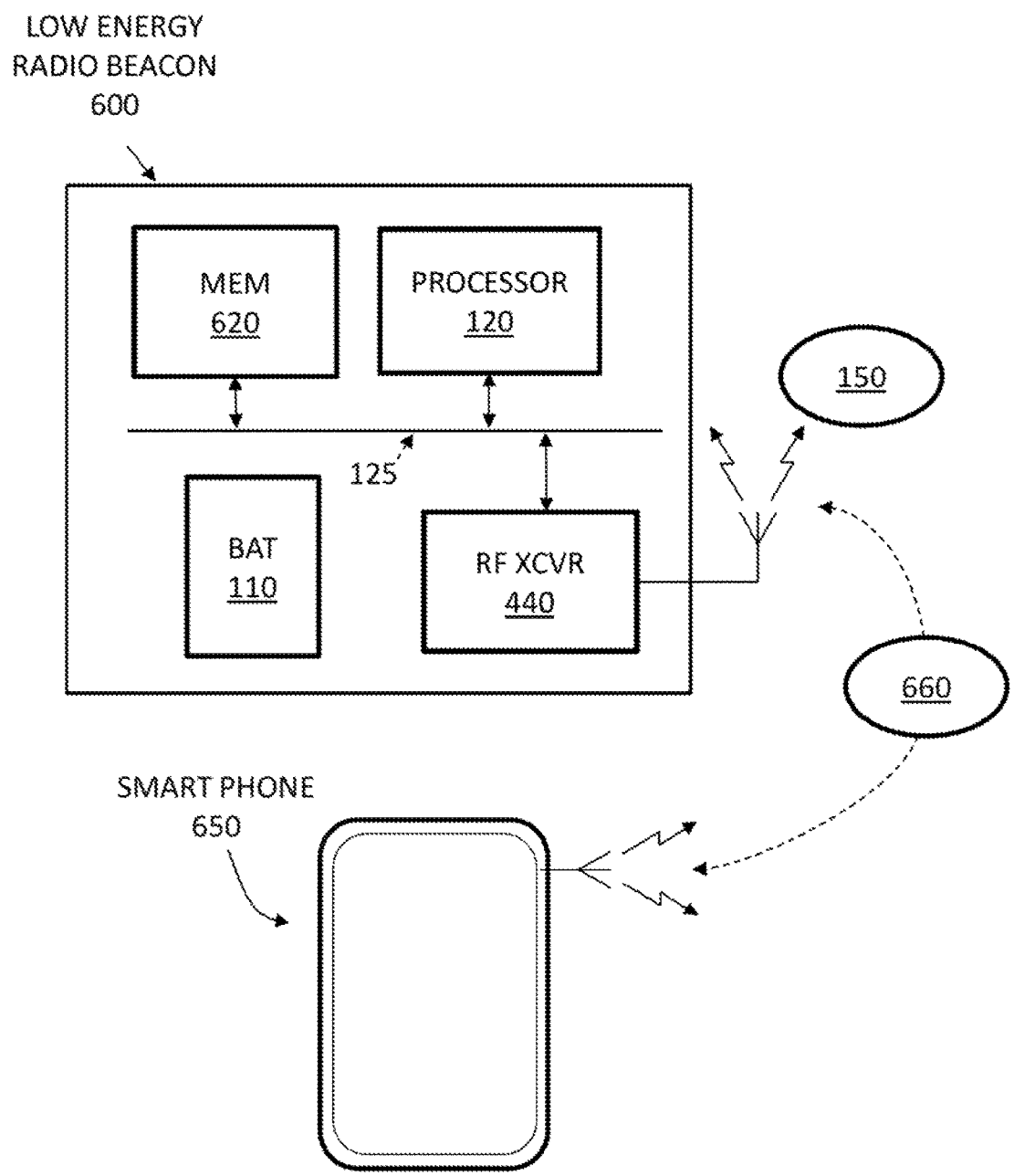
FIG. 6 shows a schematic diagram of a low energy radio beacon able to receive and transmit radio signals, a smartphone with radio transceiver, and transmission messages associated with the two devices.

FIG. 6 shows a schematic diagram of an embodiment using radio transmission packets 660 transmitted from a mobile device 650 to detect presence. The mobile device 650, for example, may be any wireless mobile device, such as a smartphone, cellphone, laptop, tablet, smart watch, digital glasses, fitness monitor, PDA, tracking device, or some other portable or moveable device capable of transmitting, and optionally receiving, wireless signals. This approach works particular well if the mobile device 650 has installed an application programmed to work with the low energy radio beacons 600 installed in the space. The processor instructions as stored on memory device 620 differ from the instructions as stored on memory device 130 as shown in FIG. 1 in that the low energy radio beacons 600 may be configured to only activate their location broadcasts when requested by the application on the mobile device 650. The application may even request to selectively activate certain beacons based on different use cases. For example, if the application is used only for finding a way through a museum, there is no need to activate the beacons associated with art objects, only beacons installed in central locations may be activated. Alternatively, an application on the mobile device 650 might be requested to get information only from selected beacons which are of interest to a user.

With use of a mobile device 650, for example, the low energy radio beacon 600 may wake up at regular times and check to determine if any mobile devices 650 are in its proximity, e.g., as indicated by the presence of radio transmission packets 660, and are interested in its services. If the low energy radio beacon 600 does not receive a radio transmission packets 660, the low energy radio beacon 600 may return to sleep mode.

Figure 7:
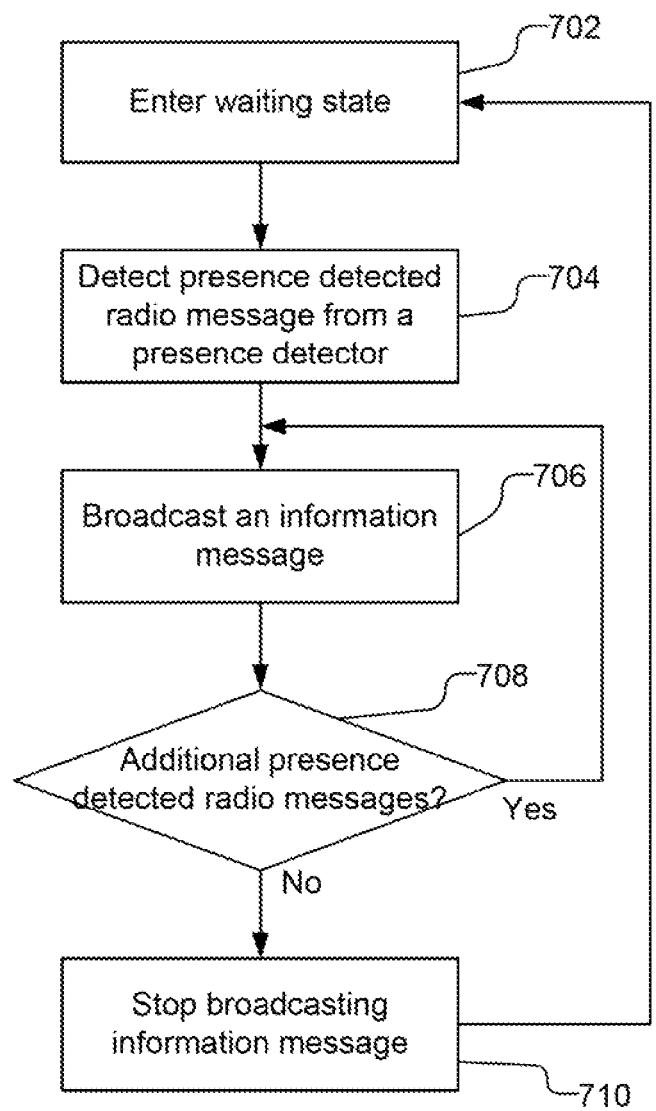
FIG. 7 shows a flow diagram illustrating how a low energy beacon processes information received from the radio equipped presence detectors.

FIG. 7 shows a flow diagram illustrating how a low energy presence activated radio beacon processes information received from the radio equipped presence detectors. In normal operation, the low energy radio beacon enters a waiting state (702). In the waiting state, power consumption may be reduced or minimized in the low energy radio beacon, e.g., by periodically awakening from sleep mode with the radio transceiver in receive mode. The low energy radio beacon may detect a presence detected radio message from a remote radio equipped presence detector (704) by receiving the presence detected radio message with the radio transceiver, as discussed above. When a presence detected radio message is detected, the radio transceiver will start broadcasting an information message (706). The information message may be, e.g., an amount of information associated with the radio beacon device such as information pertaining to the location of the beacon device or information related to an object associated with the radio beacon or a current status of the radio beacon device. The information message may be broadcast for a predetermined duration, e.g., an amount of time controlled by a timer. If additional presence detected radio messages are received (708), the timer used to control the duration of the broadcast of the information message may be reset, e.g., illustrated in the flow chart as the process returning to block 706. If no additional presence detected radio messages are received (708) and the broadcast duration timer has lapsed, the broadcast of the information message is stopped (710), and the radio beacon device re-enters the waiting state (702). In some embodiments, the presence activated radio beacon may additionally detect a message from a mobile device, and in response begin broadcasting the information message. When no additional messages are detected from the mobile device, the broadcast of the information message may be stopped and the presence activated radio beacon may reenter the waiting state. For example, the presence activated radio beacon may broadcast the information message as long as the message from the mobile device is detected and for a predetermined time thereafter.

Figure 8:
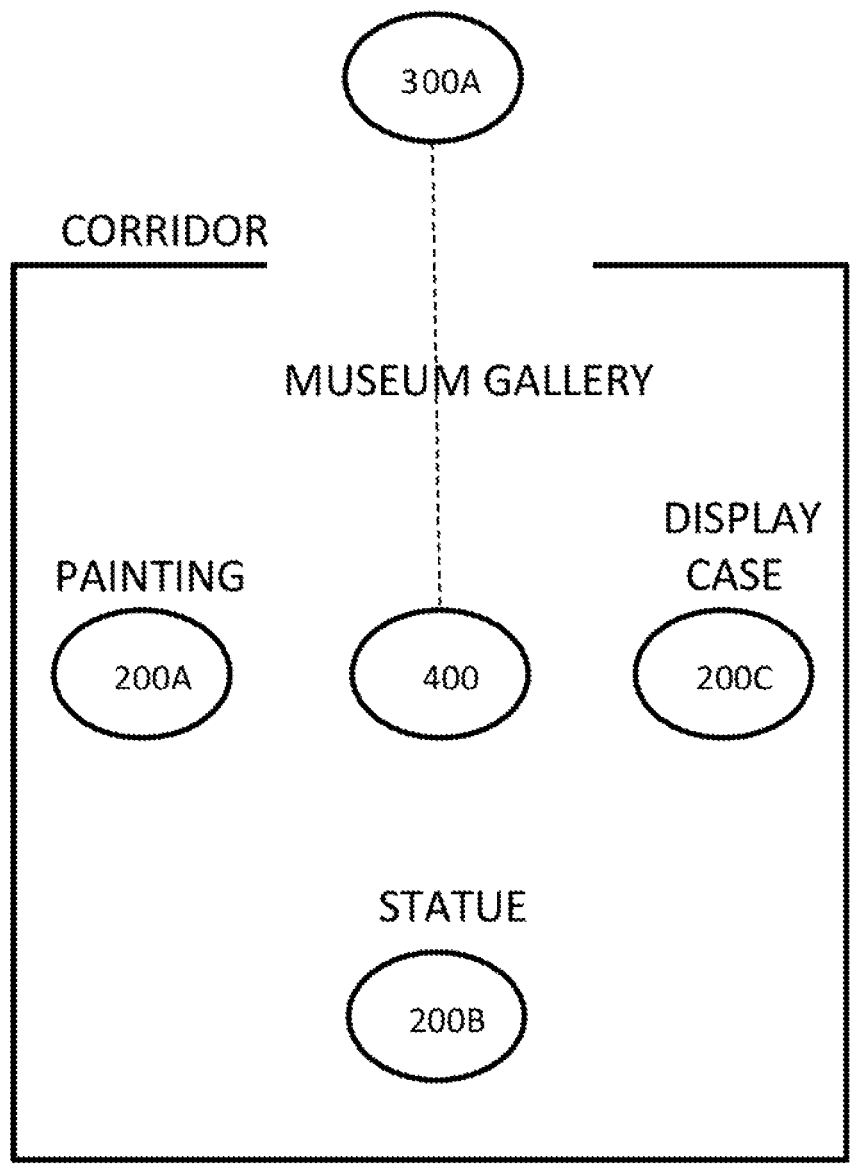
FIG. 8 illustrates a use case for low energy beacons in a museum gallery.

FIG. 8 illustrates a use case for low energy beacons in a museum gallery using low energy radio beacons 200A, 200B, and 200C (sometimes collectively referred to as radio beacons 200) with integrated presence detectors, and one low energy beacon 400 associated with a detached radio equipped presence detector 300A. The presence detector 300A is mounted in a corridor in the gallery, and will send a presence detection message to radio beacon 400 if a person is approaching the gallery. When the radio beacon 400 starts broadcasting, a mobile device, such as a smartphone, with that person will receive location information from the radio beacon 400 and might trigger some actions on the mobile device, e.g., if enabled by the user. In a museum use case, for example, the user may install a museum application on the mobile device and indicate interest in new objects in the museum, and the application may provide an audio signal to indicate that there is a new painting located in a room that the user has entered, e.g., museum gallery in FIG. 8.

In museum gallery, there are also three other low energy radio beacons 200, all three with an integrated short range presence detector, and each corresponding to a different object. If a person enters the room and walks up to one of the three objects, the corresponding low energy radio beacon 200 detects the presence of the person and provides a digital radio message to the application on the person's mobile device providing detailed information for the museum object to which the person is proximate.

Although certain specific embodiments are described above for instructional purposes, the teachings of this patent document have general applicability and are not limited to the specific embodiments above.

Radio transmission presence messages from a presence detector might not be directly received by a low energy beacon, but might be rebroadcast by other wireless radios part of a mesh network. Radio transmissions might also pass through gateways, and the gateways might translate the message from one radio protocol to another protocol. Presence detectors might also be attached to a wired network, and the radio transmitted presence detection messages will be received through support of a gateway only. Presence detection might also be implemented using cameras, connected to power, and might selectively activate low energy radio beacons based on the location and direction of occupants detected. Alternatively, presence may be detected by vibration sensors (such as accelerometers), audio sensors, or by inductive sensors or contact connections associated with objects such as merchandise that have been approached or moved by a shopper.

Accordingly, various modifications, adaptations, and combinations of various features of the described embodiments can be practiced without departing from the scope of the invention as set forth in the claims.

What is claimed is:

1. A presence activated radio beacon device comprising:
   a presence detector configured to detect presence of an occupant in its proximity;
   a radio transmitter capable of broadcasting information associated with location or status of the presence activated radio beacon device;
   a memory configured to store an amount of information associated with the location or the status of the presence activated radio beacon device; and
   a processor configured to detect presence signals from the presence detector and to activate the radio transmitter to enable transmission from the radio transmitter in response to detection of presence signals as long as a presence is detected and for a finite predetermined time thereafter.

2. The presence activated radio beacon device of claim 1, wherein the processor is configured to configure the radio transmitter with a message to transmit based on the information or the status stored in the memory.

3. The presence activated radio beacon device of claim 1, wherein the radio transmitter is a radio transceiver capable of receiving wireless signals and wherein the processor is further configured to alter the amount of information stored in memory in response to the wireless signals received by the radio transceiver.

4. The presence activated radio beacon device of claim 1, wherein the processor is further configured to deactivate the radio transmitter and to go into a sleep mode until the presence is detected by the presence detector.

5. The presence activated radio beacon device of claim 1, wherein the presence detector comprises one of a Passive Infrared (PIR) motion sensor, camera, vibration sensor, audio sensor, inductive sensor, contact sensor.

6. The presence activated radio beacon device of claim 1, wherein the transmission from the radio transmitter comprises a presence message.

7. A presence activated radio beacon device comprising:
   a radio transceiver capable of receiving presence detection information messages from a radio equipped presence sensor in proximity to the presence activated radio beacon device and capable of broadcasting information messages;
   a memory configured to store an amount of information associated with the presence activated radio beacon device;
   a processor configured to process messages received by the radio transceiver, detect a presence detection information message from the radio equipped presence sensor, and activate the radio transceiver to enable transmission of an information message from the radio transceiver in response to the detection of the presence detection information message as long as the presence detection information message is detected and for a finite predetermined time thereafter.

8. The presence activated radio beacon device of claim 7, wherein the processor is further configured to: configure the radio transceiver with the information message to transmit based on the amount of information stored in the memory or based on a current status of the presence activated radio beacon device.

9. The presence activated radio beacon device of claim 7, wherein the radio transceiver is capable of receiving wireless signals and wherein the processor is further configured to alter the amount of information stored in memory in response to the wireless signals received by the radio transceiver.

10. The presence activated radio beacon device of claim 7, wherein the processor is further configured to place the radio transceiver in receive mode and to go into a sleep mode until the presence is detected by the presence detector.

11. The presence activated radio beacon device of claim 7, wherein the processor is further configured to synchronize communication slots with the presence detector and to place the radio transceiver in sleep mode outside of the communication slots.

12. The presence activated radio beacon device of claim 7, wherein the presence detector comprises one of a Passive Infrared (PIR) motion sensor, camera, vibration sensor, audio sensor, inductive sensor, contact sensor.

13. The presence activated radio beacon device of claim 7, wherein the information message transmitted from the radio transceiver comprises a presence detection information message received from the radio equipped presence sensor.

14. A presence activated radio beacon device comprising:
a radio transceiver capable of receiving messages from mobile devices;
a memory configured to store an amount of information associated with the presence activated radio beacon device; and
a processor configured to process messages received by the radio transceiver, detect messages from a mobile device, configure the radio transceiver with an information message to transmit based on the amount of information stored in the memory, and activate the radio transceiver to enable transmission of the information message from the radio transceiver in response to the detection of a message from the mobile device, as long as the message from the mobile device is detected and for a finite predetermined time thereafter.

15. The presence activated radio beacon device of claim 14, wherein the radio transceiver is capable of receiving wireless signals and wherein the processor is further configured to alter the amount of information stored in memory in response to the wireless signals received by the radio transceiver.

16. The presence activated radio beacon device of claim 14, wherein the processor is further configured to place the radio transceiver in receive mode and to go into a sleep mode until the detection of a message from the mobile device.

17. The presence activated radio beacon device of claim 14, wherein the information message transmitted from the radio transceiver comprises a presence detection information message received from the radio equipped presence sensor.

18. A method of activating a presence activated radio beacon device, the method comprising:
entering a waiting state controlled by a processor;
detecting with a radio transceiver a presence detected radio message from a remote radio equipped presence sensor;
exiting the waiting state controlled by the processor;
broadcasting with the radio transceiver an information message in response to detecting the presence detected radio message, wherein broadcasting the information message comprises broadcasting the information message as long as the presence detected radio message is detected and for a finite predetermined time thereafter;
stopping the broadcast of the information message after the predetermined when no additional presence detected radio message is detected; and
re-entering the waiting state controlled by the processor.

19. The method of claim 18, wherein in the waiting state the presence activated radio beacon device periodically awakens from sleep mode with a radio transceiver in receive mode.

20. The method of claim 18, wherein the information message comprises at least one of information pertaining to a location of the presence activated radio beacon device, to an object associated with the presence activated radio beacon device, and a current status of the presence activated radio beacon device, or a combination thereof.

21. The method of claim 18, further comprising:
detecting a message from a mobile device;
broadcasting the information message in response to detecting the message from the mobile device;
stopping the broadcast of the information message when no additional messages are detected from the mobile device; and
re-entering the waiting state.

22. The method of claim 21, wherein broadcasting the information message in response to detecting the message from the mobile device comprises broadcasting the information message as long as the message from the mobile device is detected and for a predetermined time thereafter.

* * * * *